(12) United States Patent
Greene et al.

(10) Patent No.: US 7,041,868 B2
(45) Date of Patent: May 9, 2006

(54) BIOABSORBABLE WOUND DRESSING

(75) Inventors: Sharon L. Greene, Canton, GA (US); Archel A. Ambrosio, San Antonio, TX (US); Rosann M. Matthews Kaylor, Cumming, GA (US); Dave A. Soerens, Neenah, WI (US); Sohail Malik, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 764 days.

(21) Appl. No.: 10/026,292

(22) Filed: Dec. 19, 2001

(65) Prior Publication Data

US 2002/0111576 A1 Aug. 15, 2002

Related U.S. Application Data

(60) Provisional application No. 60/259,120, filed on Dec. 29, 2000.

(51) Int. Cl.
*A61F 5/00* (2006.01)
*A61L 15/16* (2006.01)

(52) U.S. Cl. .................................. 602/48; 424/444
(58) Field of Classification Search ................ 424/444, 424/443, 445; 602/41–59; 604/305–308
See application file for complete search history.

(56) References Cited

U.S. PATENT DOCUMENTS

| | | | |
|---|---|---|---|
| 3,800,792 A | 4/1974 | McKnight et al. ........... | 128/156 |
| 3,875,937 A | 4/1975 | Schmitt et al. .............. | 128/156 |
| 3,903,882 A | 9/1975 | Augurt ......................... | 128/155 |
| 4,060,081 A | 11/1977 | Yannas et al. ............... | 128/156 |
| 4,074,366 A | 2/1978 | Capozza ......................... | 3/1 |
| 4,178,361 A | 12/1979 | Cohen et al. ................. | 424/22 |
| 4,265,233 A | 5/1981 | Sugitachi et al. ........... | 128/156 |
| 4,407,787 A | 10/1983 | Stemberger ................... | 424/28 |
| 4,570,629 A | 2/1986 | Widra ........................ | 128/156 |
| 4,683,142 A | 7/1987 | Zimmermann et al. ........ | 427/2 |
| 4,703,108 A | 10/1987 | Silver et al. ................ | 530/356 |
| 4,759,354 A | 7/1988 | Quarfoot .................... | 128/156 |
| 4,834,734 A | 5/1989 | Morganti .................... | 604/368 |
| 4,837,285 A | 6/1989 | Berg et al. .................. | 530/356 |
| 4,841,962 A | 6/1989 | Berg et al. .................. | 128/156 |
| 4,947,840 A | 8/1990 | Yannas et al. .............. | 128/156 |
| 4,970,298 A | 11/1990 | Silver et al. ................ | 530/356 |
| 4,973,466 A | 11/1990 | Reich ........................ | 424/426 |

(Continued)

FOREIGN PATENT DOCUMENTS

| | | | |
|---|---|---|---|
| CA | 2109672 | | 11/1993 |
| EP | 0099758 A2 | | 7/1983 |
| EP | 0227955 A2 | | 7/1983 |
| WO | WO 97/46265 | | 12/1997 |
| WO | WO 00/16821 | * | 3/2000 |

OTHER PUBLICATIONS

Publication: Poly (D, L–lactic acid)/poly (e–caprolactone) blend membranes: preparation and morphological characterization; Journal of Materials Science 35 (2000) 1615–1622.

*Primary Examiner*—Weilun Lo
*Assistant Examiner*—Linh Truong
(74) *Attorney, Agent, or Firm*—Nelson, Mullins, Riley & Scarborough, LLP

(57) ABSTRACT

A wound dressing includes a first layer located adjacent the wound and which comprises a material that is bioabsorbable, porous and adapted for serving as a scaffold for cell attachment and proliferation; and a second layer which is in contact with the first layer and which comprises an absorbent, gel forming material adapted for serving as a barrier to cell adhesion and penetration. A method of treating a wound with the dressing is also disclosed.

23 Claims, 6 Drawing Sheets

U.S. PATENT DOCUMENTS

| | | | |
|---|---|---|---|
| 5,116,824 A | 5/1992 | Miyata et al. | 514/55 |
| 5,460,939 A | 10/1995 | Hansbrough et al. | 435/1.1 |
| 5,480,717 A | 1/1996 | Kundel | 428/338 |
| 5,489,304 A | 2/1996 | Orgill et al. | 623/15 |
| 5,536,656 A | 7/1996 | Kemp et al. | 435/240.23 |
| 5,593,395 A | 1/1997 | Martz | 604/304 |
| 5,604,200 A | 2/1997 | Taylor-McCord | 514/8 |
| 5,658,582 A * | 8/1997 | Dorigatti et al. | 424/443 |
| 5,674,523 A | 10/1997 | Cartmell et al. | 424/445 |
| 5,679,371 A | 10/1997 | Tanihara et al. | 424/443 |
| 5,698,322 A | 12/1997 | Tsai et al. | 428/373 |
| 5,733,337 A | 3/1998 | Carr, Jr. et al. | 623/11 |
| 5,759,570 A | 6/1998 | Arnold | 424/443 |
| 5,766,631 A | 6/1998 | Arnold | 424/486 |
| 5,830,708 A | 11/1998 | Naughton | 435/70.1 |
| 5,856,367 A | 1/1999 | Barrows et al. | 521/64 |
| 5,863,984 A | 1/1999 | Doillon et al. | 525/54.1 |
| 5,955,578 A | 9/1999 | Pierschbacher et al. | 530/345 |
| 6,039,940 A | 3/2000 | Perrault et al. | 424/78.06 |
| 6,135,987 A | 10/2000 | Tsai et al. | 604/365 |
| 6,596,304 B1 * | 7/2003 | Bayon et al. | 424/444 |

* cited by examiner

BIOABSORBABLE WOUND DRESSING

The present application claims the benefit of U.S. Provisional Application Serial No. 60/259,120 filed Dec. 29, 2000, which is incorporated herein by reference thereto.

BACKGROUND OF THE INVENTION

(1) Field of the Invention

The present invention relates to wound dressings, and more particularly to multi-layer wound dressings having an element that is bioabsorbable.

(2) Description of the Related Art

The management and treatment of external wounds and of internal traumas that are consequences of surgery are areas of intense research and commercial interest, and areas in which recent improvements have significantly improved the quality of life of patients.

Chronic wounds remain one of the most difficult and costliest chronic conditions to treat. These types of wounds also have an insidious effect on the lives of the people that suffer from them. The most common complaints of home-bound patients involve their limited mobility and the feeling of being isolated. See, e.g., Neil, J. A. et al., *Ostomy/Wound Management*, 46:28–38 (2000). Many of these patients withdraw from life and some feel like they are vegetating. Therefore, in addition to the financial burden placed on such patients and upon the healthcare system, there is also a large psychosocial cost associated with chronic wounds.

The current protocol for treatment of chronic wounds typically involves debridement followed by covering the wound with typical moist dressings such as hydrocolloids, hydrogels, alginates and the like. Some of these types of dressings are described in, for example, U.S. Pat. No. 4,570,629, which describes a hydrogel membrane formed from biodegradable copolyelectrolytes. Other such formulations are described in U.S. Pat. Nos. 4,973,466, 5,604,200, 5,679,371 and 6,039,940. U.S. Pat. No. 5,674,523 combines a hydrogel layer with a vapor permeable bacterial barrier.

The use of collagen in wound dressings has been the focus of much work. Such dressings have been fabricated as compressed foam (U.S. Pat. No. 3,800,792), a two-layer dressing of a crosslinked composite of collagen and mucopolysaccharide covered with a moisture transmission control membrane (U.S. Pat. No. 4,060,081), and a dressing made from collagen in combination with a resorbable biopolymer such as fibrinogen (U.S. Pat. No. 4,407,787). Other collagen-based dressings are described in U.S. Pat. Nos. 4,703,108, 4,759,354, 4,834,734, 4,837,285, 4,841,962, 4,970,298, 5,116,824, 5,536,656, 5,579,570, 5,733,337 and 5,863,984.

In U.S. Pat. No. 4,947,840, the use of collagen, as well as synthetic polymers, such as polylactides or polyglycolic acids, was described for the production of biodegradable templates for regeneration of tissues. Factors such as pore size of the template and pore volume fraction were shown to control the rate of wound contraction—especially for implant-containing wounds. U.S. Pat. No. 5,856,367 describes a method of producing biocompatible, porous matrices containing a bioabsorbable matrix (collagen is used to form the matrix), where a volume orientation aid is employed to obtain pore formation.

Dressings and compositions that provide drug delivery features are described in, for example, U.S. Pat. No. 4,178,361, which describes a sustained release pharmaceutical composition in a hydrogel-forming matrix. U.S. Pat. No. 4,683,142 describes a multilayered sheet material consisting of a glycoprotein matrix containing substances which cause blood coagulation, and U.S. Pat. No. 5,593,395 describes a multi-layer dressing having an adhesive release sheet containing a topical drug or medicine.

The use of bioabsorbable synthetic materials in wound dressings has been reported in several publications, such as the use of fabric or sponge made from polyglycolic acid (U.S. Patent No. 3,875,937), or polyglycolic acid on which a vapor permeable film had been deposited (U.S. Pat. No. 3,903,882). The use of an enzymatically degradable material, poly(N-acetyl-D-glucosamine), as sutures, absorbable fabrics, gauze, bone splints and the like has been described in U.S. Pat. No. 4,074,336. U.S. Pat. No. 5,955,578 describes a matrix containing attachment peptides of less than 30 amino acids, which are conjugated to a biodegradable polymer, such as, for example, hyaluronic acid.

The use of beneficial coatings on dressing materials has also been reported. For example, U.S. Pat. No. 4,265,233 describes a method of fixing blood coagulation factor XIII to a dressing material to aid in wound healing.

More advanced forms of treatment, such as the use of growth factor gels and artificial skin type products recently have been introduced with some degree of success. While some of the products have produced significantly better outcomes than the typical dressings, they can be very costly and still do not cause healing in a significant number of wounds. See, e.g., *Reuters Medical News*, (Jun. 15, 2000) at www.upmc.com/reuters/prof/2000/06/06.15/20000615clin004.html, and Brem, H. et al., *Arch. Surg.* 135:627–634 (2000).

One tissue-engineered product utilizes cells, such as fibroblast cells, that are grown on a bovine collagen scaffold to mimic the dermis of the skin. Keratinocytes are grown on top of the dermal layer to form the epidermal layer. These procedures are carried out in an in vitro environment. The complexity of the production process and the raw materials that are required cause the product to be relatively costly, and because it contains living cells, it requires special packaging and has a relatively limited shelf life. See, e.g., Parenteau, N., *Sci. American*, 280(4):83–84 (1999). Another living skin replacement is composed of living stromal tissue, such as fibroblasts, cultured upon a three-dimensional framework and a transitional covering. (U.S. Pat. No. 5,460,939). The use of extracellular matrix material deposited by a culture of stromal cells grown on a support matrix is described in U.S. Pat. No. 5,830,708.

Another method of skin regeneration includes covering the wound with a collagen glycosaminoglycan matrix, allowing infiltration of the matrix by mesenchymal cells and blood vessels and applying a cultured epithelial autograft sheet grown from epidermal cells taken from the same patient at a wound-free site on the patient's body surface. (U.S. Pat. No. 5,489,304).

Although treatment methods that provide artificial skin that contains living cells, or is prepared from cell culture, are often effective and remain very promising, their application can also be time-consuming and expensive. Moreover, some of these techniques and products are limited to use only on the patient from which the cells were obtained. Therefore, methods of wound treatment that are relatively inexpensive, easy to apply, and can be applied to any patient quickly after the wound has been incurred, would be useful.

Several new dressings have shown promise in helping to overcome some of these defects. For example, EP 0 099 758 A2 describes a composite, multilayered wound dressing having a semipermeable membrane, a permeable supporting membrane, and a biodegradable tissue interface. A dressing described in EP 0 227 955 A2 is similar. However, in neither patent is there an indication that the biodegradable tissue interface layer serves as a scaffold for cell growth.

Canadian Patent No. 2,109,672 describes a multilayer wound dressing that includes a wound contact layer of biocompatible material, a molecular filtration membrane having a maximum pore size of about 0.5 microns, and an absorbent layer atop the molecular filtration membrane. In use, the membrane retains biopolymers and wound healing factors at the wound surface while excluding bacteria and allowing rapid egress of wound exudate into the absorbent layer. The wound contact layer is typically formed from a bioabsorbable material that forms a bioabsorbable gel upon contact with wound exudate. However, as in the dressings described just above, the wound contact layer of this dressing apparently does not serve as a scaffold for cell growth.

WO 97/46,265 describes a multi-layered wound dressing that includes a fluid permeable and bioresorbable lower section that is adjacent the wound and that promotes healing of the wound. The bioresorbable material can be made from biodegradable esters such as poly(3-hydroxybutyrate). The use of a protein-free bioresorbable polymer is said to be advantageous because it appears to stimulate healing by stimulating macrophages and working as a scaffold for cell growth. The polymer is also said to stimulate vascularization and microcirculation. The dressing includes an upper section that is permeable to vapor and impermeable to bacteria. An intermediate section of, for example, cellulose fibers, polyacrylic acids, or preferably a hydrocolloid, may also be added to serve as an absorbent layer. There is no indication that this section is resistant to adhesion or penetration by growing cells of the healing tissue and it could be expected that the large pores of a cellulose fiber structure might invite such penetration. Therefore, when the dressing is changed after being in place for an extended period, either the intermediate layer must be left in place, or some damage to any cells or tissue that have penetrated the intermediate layer would be expected.

Despite these advances, there is still a need for a dressing that accelerates wound healing, avoids trauma and disturbance of healing due to removal or replacement of the dressing, provides management of wound exudate, can be stored for extended periods of time and is easily used on any patient.

It is to such needs that the present invention is directed.

SUMMARY OF THE INVENTION

Briefly, therefore, the present invention is directed to a novel wound dressing comprising a first layer located adjacent the wound and which comprises a material that is bioabsorbable, porous and adapted for serving as a scaffold for cell attachment and proliferation; and a second layer which is in contact with the first layer and which comprises an absorbent, gel forming material adapted for serving as a barrier to cell adhesion and penetration.

The present invention is also directed to a novel wound dressing comprising a first layer located adjacent the wound and which comprises a material that is bioabsorbable, porous and adapted for serving as a scaffold for cell attachment and proliferation; a second layer comprising a transparent film of a breathable material that can transmit liquid peripherally to the edges of said second layer, but which is adapted for serving as a barrier to cell adhesion and penetration; and a third layer which is in contact with the second layer and which comprises an absorbent material.

The present invention is also directed to a novel wound dressing which is similar to the dressing described just above, except that the materials comprising the second layer and the third layer are reversed.

The present invention is also directed to a novel method for treating a wound comprising applying to the wound a wound dressing comprising a first layer located adjacent the wound and which comprises a material that is bioabsorbable, porous and adapted for serving as a scaffold for cell attachment and proliferation; and a second layer which is in contact with the first layer and which comprises an absorbent, gel forming material adapted for serving as a barrier to cell adhesion and penetration.

Among the several advantages found to be achieved by the present invention, therefore, may be noted the provision of a dressing that accelerates wound healing, the provision of a dressing that avoids trauma and disturbance of healing due to removal or replacement of the dressing, the provision of a dressing that provides management of wound exudate, and the provision of a dressing that can be stored for extended periods of time and is easily used on any patient.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

Figure 1:
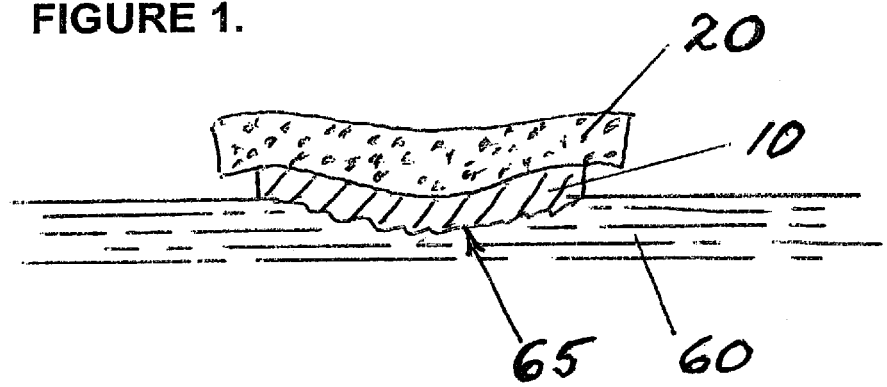
FIG. 1 illustrates a cross-sectional view of a dressing of the present invention having a bioabsorbable and porous first layer that is adapted for serving as a scaffold for cell attachment and proliferation disposed adjacent a wound bed and having an absorbent, gel-forming second layer of a material adapted for serving as a barrier to cell adhesion and penetration.

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

In accordance with the present invention, it has been discovered that a multilayer wound dressing can be made that accelerates wound healing by having a first layer that is located adjacent the wound when the dressing is in use, and where the first layer is a bioabsorbable and porous material that is adapted for serving as scaffold for new cells to attach and proliferate. This material may be referred to herein as "bioabsorbable scaffold material", or "scaffold material". This layer can remain in place on the wound bed throughout the healing process, and is absorbed and replaced by new tissue. During healing, the first layer also transmits wound exudate from the wound bed to a second layer, which is in contact with the first layer. The second layer can be a material that is absorbent to liquid, but is adapted for serving as a barrier for cell adhesion and penetration by growing cells and larger proteins in wound exudate. This material may be referred to herein as "absorbent barrier material". Besides absorbing wound exudate and inhibiting the loss of beneficial growth factors from the scaffold material, the second layer can act as a reservoir for liquids to hydrate the wound. The features of non-adhesion and resistance to penetration by cells provide the important advantage that the absorbent barrier material—and any subsequent layer—is easily removed and/or replaced as needed without disturbing the scaffold material and without causing trauma to growing cells or tissue.

In an alternative embodiment, the feature of serving as a barrier for cell attachment and growth can be provided by the first layer—the scaffold material itself—by the use of a material in which the size of the pores that are located next to the wound bed are large enough for cell penetration and growth, but the size of the pores at or near the opposite side of the layer are sufficiently small to prevent the penetration of such cells. A first layer of this type may be placed in contact with an absorbent material that does not necessarily have the cell barrier property.

If desirable, the second layer can be in contact with a third layer that can be a breathable film that can serve as a barrier to the entry of bacteria into the wound bed.

In another embodiment, the second layer can be a film of a transparent material that is capable of transport of liquid, but which can serve as a barrier for cell penetration and adhesion and as a barrier for microbial infection.

The novel dressing is easy to use. It does not require surgery to apply, and can be configured for use on both shallow wounds and deep cavity wounds. The dressing has no living cells or rapidly degraded components and, accordingly, is easily stored and can be stored for a period of up to one or two years. Because the subject dressing does not require living cells or expensive biologically-derived chemicals, it is also relatively easy and inexpensive to produce.

The first layer of the subject dressing is a bioabsorbable material that is porous and adapted for serving as a scaffold for cell attachment and proliferation. This bioabsorbable scaffold material can also serve as a reservoir for wound exudate, thereby retaining beneficial growth factors contained in that fluid. The growth factors can be kept in contact with the wound bed and thereby continue to provide benefit to the healing process. The material that is used for the scaffold material is adapted to serve as a scaffold for cell growth by providing a surface for cell attachment while the interconnected pores of the material provide channels for in-growth of new cells and eventually new tissue. And, because the scaffold material is bioabsorbable, it will not need to be removed or disturbed during wound healing and will eventually break down and be replaced by new tissue.

As used herein, the term "layer" should be understood to describe almost any shape or form of a material, but commonly will refer to a material that is in the shape of a continuous or discontinuous sheet or film of almost any thickness and degree of regularity or irregularity. The designation of a "first layer", "second layer", and the like, is meant to describe the location of a material relative to the wound bed. For example, the material located adjacent the wound bed and in contact with it is termed the "first layer". The material that is placed on top of the first layer (proceeding in a direction away from the wound bed) is termed the "second layer", and so on. A layer may comprise one material, or two or more materials.

As that term is used herein, "bioabsorbable" describes the property of a material to break down when the material is exposed to conditions that are typical of those present in a wound bed into degradation products that can be removed from the wound site within a period that roughly coincides with the period of wound healing. Such degradation products can be absorbed into the body of the patient or can be transmitted into another layer of the dressing. The period of wound healing is to be understood to be the period of time measured from the application of a dressing to the time that the wound is substantially healed. This period can range from a period of several days for simple skin abrasions on rapidly healing patients, to several months for chronic wounds on patients that heal more slowly. It is intended that the subject dressing can be fabricated so that the time required for bioabsorption of the scaffold material can be tailored to match the type of wound and the time necessary for healing. For example, in some dressings of the subject invention, the scaffold material may be designed to degrade within a period of one week, while in other dressings it may be designed to degrade within a period of one-to-three months, or even longer if desirable.

The bioabsorbable scaffold material can be produced from any material that is bioabsorbable and that also meets the other criteria of that material as those criteria are described above. The scaffold material can be formed from bioabsorbable polymers such as (but not limited to) polymers of lactic and glycolic acids, copolymers of lactic and glycolic acids, poly(ether-co-esters), poly(hydroxybutyrate), copolymers of lactic acid and $\epsilon$-aminocaproic acid, lactide polymers, copolymers of poly(hydroxybutyrate) and 3-hydroxyvalerate, polyesters of succinic acid, poly(N-acetyl-D-glucosamine), cross-linked hyaluronic acid and cross-linked collagen.

The bioabsorbable scaffold material that is useful in the present invention can dissolve in exudate at rates equal to, or slightly slower than the rate of wound healing. The rates of bioabsorption of the scaffold material can be tailored, if desired, according to the expected time of healing of the wound to which it is to be applied. For example, a scaffold material that is bioabsorbed within one or two weeks may be particularly useful for a rapidly healing wound, while a scaffold that is bioabsorbed within approximately 1–2 months can be used for chronic wounds and wounds that require longer healing times. The rate of bioabsorption of the scaffold material can be controlled by the selection of the type of polymers that form the material, and by selection of such variables as chain length, degree of cross-linking, degree of substitution with substituents, selection of substituents that can be grafted to the polymer, and other factors that are well known to those having skill in the art.

The scaffold material can be formed from woven or nonwoven fabric, and can particularly be formed from meltblown and spunbonded fibers. As used herein, the term "nonwoven" fabric refers to a fabric that has a structure of individual fibers or filaments which are interlaid, but not in an identifiable repeating manner.

As used herein, the term "spunbond fibers" refers to fibers which are formed by extruding molten thermoplastic material as filaments from a plurality of fine, usually circular capillaries of a spinnerette with the diameter of the extruded filaments then being rapidly reduced as by, for example, in U.S. Pat. Nos. 4,340,563, 3,692,618, 3,802,817, 3,338,992, 3,909,009 and 3,542,615.

As used herein, the term "meltblown fibers" refers to fibers which are formed by extruding molten thermoplastic material as filaments from a plurality of fine, usually circular, die capillaries as molten threads or filaments into a high velocity, usually heated gas (e.g., air) stream which attenuates the filaments of molten thermoplastic material to reduce their diameter. Thereafter, the meltblown fibers are carried by the high velocity gas stream and are deposited on a collecting surface to form a fabric of randomly disbursed meltblown fibers. Meltblowing is described, for example, in U.S. Pat. Nos. 4,307,143 and 4,663,220.

The first layer can also be a foam or any 3-dimensional porous structure. Further information about the formation of poly(D,L-lactic acid)/poly($\epsilon$-caprolactone) blend membranes suitable for use in the present invention are given by Asian et al., in *J. Mater. Sci.*, 35:1615–1622 (2000). The preparation of fibers from bioabsorbable polymers is described in U.S. Pat. Nos. 5,698,322 and 6,135,987.

The scaffold material is porous, and has interconnecting pores having a pore size in the range of about 50–400 microns. It is believed that pores of this size range can accommodate penetration by cells and can support the growth and proliferation of cells, followed by vascularization and tissue development.

The scaffold material can be surface-modified with biomolecules such as (but not limited to) hyaluronans, collagen, laminin, fibronectin, growth factors, integrins (Arg-Gly-Asp; i.e., RGD's), and the like, or by sodium hyaluronate and/or chitosan niacinamide ascorbate, which are believed to enhance cell migration and proliferation, or any combination thereof. The scaffold can also be impregnated with these and other bioactive agents such as drugs, vitamins, growth factors, therapeutic peptides, and the like. In addition, drugs that would alleviate pain may also be incorporated into the first layer.

The scaffold material can also be selected to encourage epithelialization, granulation and general healing. Without being bound by this or any other theory, the inventors believe that when the first layer comprises polymers of, for example, lactic acid, the lactic acid degradation products that are formed can promote angiogenesis. Moreover, it is believed that the inclusion of hyaluronic acid in the first layer allows the optimal delivery of lactic acid, and that the combined acidity caused by the degrading scaffold and the hyaluronan provides an environment that is detrimental to bacteria, thus preventing bacterial contamination. In addition, it is believed that an acidic environment promotes faster wound healing.

Hyaluronic acid can be a component of the first layer as a fiber coating or it can merely be present as a separate component of the first layer. The use of hyaluronan gel is believed to allow for the optimal delivery of lactic acid to the wound (See, e.g., www.biomatrix.com/skincarepage.htm). Moreover, hyaluronans have been shown to be less allergenic than collagen, the material commonly used in most artificial skin type products. (See, e.g., *U. S. Biologically Derived Polymers for Medical Applications*, Frost and Sullivan Report, Ch. 4 (1996). It is believed that the combined acidity caused by the degrading scaffold and hyaluronan coating provides an environment that is detrimental to common bacteria, thus inhibiting bacterial contamination. In addition, it has been suggested that an acid environment promotes faster healing. Mani, R., *Wound Rep. Regen.*, 7:330–334 (1999), and that hyaluronans serve to facilitate cellular migration and division in the epidermis. See, e.g., www.glycoforum.gr.jp/science/hyaluronan/HA04/HA04E.html.

Chitosan and its derivatives have properties important in wound healing as well and can be included as components of the first layer. They are GRAS (Generally Regarded As Safe) compounds that are known to have antimicrobial properties. As mentioned above, proteins, such as collagen, laminin, fibronectin and the like, and growth factors that are known to accelerate wound healing can be included in the first layer. Integrins are dimeric proteins that help in cell adhesion. Some members of the integrin family also bind other proteins such as collagen, fibronectin and laminin—all of which are important in wound healing.

The thickness of the first layer may be about 1–2 mm, and may be thicker for deep cavity wounds.

The absorbent barrier material of the present invention is a material that is absorbent to aqueous liquids, is gel-forming when hydrated by aqueous liquids, and which is adapted for serving as a barrier to cell adhesion and penetration. This material can be a microporous gel-forming or non-adherent material that can be made more or less absorbent and breathable to suit the condition of the wound bed (dictated by the stage of wound healing or the type of wound), while also preventing the dehydration of the wound. In order to prevent wound dehydration, the absorbent barrier material must be capable of both absorbing and donating liquid.

As used herein, the terms "adapted for serving as a barrier to cell adhesion" means that the material has surface characteristics that tend to discourage adhesion by growing epithelial cells. The terms "adapted for serving as a barrier to cell penetration" means that the material provides pores that are sufficiently small to substantially prevent, or substantially reduce the in-growth of epithelial cells, or that the combination of the pore size and the surface characteristics of the material are sufficient that they substantially prevent, or substantially reduce the in-growth of epithelial cells. By "substantially prevent" and "substantially reduce" the in-growth of epithelial cells, it is meant that the barrier material can permit some small amount of cell penetration and in-growth, but not so much as to substantially disturb the surface of the healing wound when the barrier material is removed.

This absorbent barrier layer can be removed if necessary to renew the absorbent characteristics of the dressing without disturbing granulating or new epithelial tissue. Because the absorbent barrier material is microporous and/or has a surface to which cells tend not to adhere, cells cannot penetrate this second layer. As used herein, the term "microporous" means that a material has pores that are smaller in size than the cells that would be expected to attach to and penetrate the first layer of the subject dressing. In particular, the material can have pores that are in the range of less than about 10 microns in size when the material is in a hydrated state. Thus, as the scaffold material is completely replaced by new tissue, the absorbent barrier material that can act as the second layer of the dressing can be easily removed from contact with the scaffold material with minimum force, thereby preventing trauma to the newly formed tissues.

In addition, the non-adhesion and microporous properties of the absorbent barrier material may be designed to prevent absorption of proteins, such as growth factors, that are contained in the exudate and are critical to the healing process. This can be accomplished by size-exclusion due to control of the microporosity of this material. For example, the pores of the absorbent barrier material may be controlled so that they are sufficiently small as to exclude the passage of large biomolecules, such as proteins and the like.

Gel-forming polymers such as (but not limited to) polyacrylate hydrogels, polyurethane hydrogels, crosslinked polyethers, such as cross-linked poly(ethylene oxide), carboxymethylcellulose, hydrocolloid type materials, and the like can be used to form the absorbent barrier material. The layer can be composed of nonwoven fibers such as spunbonded fibers, or it can be meltblown or spunbond-meltblown-spunbond materials. The layer can also be in the form of a foam, gel, film, sheet, paste, or any structure that maintains a porosity characterized by having an average pore size of less than about 10 microns in the hydrated state. A hydrogel sheet may also be used.

Without being bound to this or any other particular theory, the inventors believe that the absorbent barrier material can absorb exudate by absorption by the polymer and also by absorption by capillary action into the micropores. In addition, this material can provide hydration to prevent drying out of the wound. Because the polymer itself can be a hydrogel, dehydration of the dressing can be prevented. The addition of an antimicrobial agent to this layer can reduce microbial contamination and infection and, because the antimicrobial agent is not in direct contact with the wound, its detrimental effect on the wound healing process can be avoided.

The absorbent barrier material can also serve as a platform for the regulated delivery of other therapeutic agents. Bioactive agents such as vitamins, proteins, peptides, growth factors, drugs, nutrients, antibiotics, and the like, can be included in the absorbent barrier material. Such compounds can be added in their pure form, or blended with adjuvants, or as a component of a controlled-release delivery formulation. The bioactive agents that are added to the absorbent barrier material can migrate to the wound bed over a period of time and thereby provide their beneficial activities for wound healing.

The breathable film that serves as a barrier to the entry of bacteria into the wound bed can be made from any material that can be formed into a film that will permit the passage of water vapor but will serve as a barrier to the passage of microorganisms. The film can also serve as a barrier to the transmission of liquid water. The film can be transparent, and can have lateral wicking ability for use in some embodiments that require peripheral transfer of exudate liquid, such as to the periphery of the dressing.

Materials that can be used to form the third layer include (without limitation) films made from elastomers such as polyurethanes, silicone or natural rubbers, poly(caprolactone), polyacrylate and polymethacrylate esters or their copolymers, and the like, which have moisture permeabilities similar to that of human skin. It is desirable that the breathable film is permeable to water vapor.

The breathable film can have pores that range from about 1 to about 8 microns in size.

In some embodiments of the subject dressing it is useful to place an adhesive on one side of one of the layers so that the dressing can be adhered to the skin of a patient. When such adhesive is required, any adhesive that is useful for this purpose can be used. Many such adhesives are known in the art.

The transparent film that is permeable to the passage of moisture, but which serves as a barrier to the entry of bacteria into the wound bed can be made from any transparent material that can be formed into a film that will permit the passage of liquids but will serve as a barrier to the passage of microorganisms. The film can be transparent, or can be of a translucent material that appears to be substantially transparent in a thin film.

Materials that can be used to form the third layer include (without limitation) films made from elastomers such as polyurethanes, silicone or natural rubbers, poly(caprolactone), polyacrylate and polymethacrylate esters or their copolymers, and the like.

The subject dressing can be formed as separate pieces that are assembled when applied to a wound, or it can be formed as a multilayer composite of two or three of the components that can be applied to a wound as a unitary dressing.

The first layer is disposed so that it can be placed adjacent the wound bed when the dressing is applied to a wound. When the first layer is in contact with a wound bed, it is common that one side of the layer is in contact with the wound bed and the opposite side faces away from the wound bed.

The second layer is in contact with the first layer. In one embodiment, shown in FIG. 1, the second layer is in contact with the side of the first layer that faces away from the wound bed. The second layer can be merely placed in contact with the first layer, or it can be lightly bound to the first layer.

In one embodiment, the first layer can be applied to the wound bed in a first step, and the first layer can then be covered by the second layer in a second step to form a two-layer dressing that has the advantageous properties of the subject dressing.

Alternatively, the first and second layers can be lightly bound together into a composite, multi-layer dressing prior to its application to the wound. Such binding may be accomplished by forming a second layer, such as for example, nonwoven fibers, directly onto one side of the first layer so that there will be points where the layers are bonded at the interface of the two layers. Thermal or ultrasonic pointbonding, as well as certain adhesives, may also be used to bond the two layers. A feature of the interface between the first and second layers is that it provides that the two layers may be easily separated by the mere act of manually pulling the second layer from the first layer without disturbing the location of the first layer on the wound bed.

As described above, when the second layer is an absorbent barrier material, the second layer will either fall off on its own or can be peeled away with the slightest force as the first layer is completely degraded. The absorbent barrier material of the second layer would also be absorbent as well as hydrating while maintaining some breathability. If necessary, it can be replaced with a new layer to renew absorbency and hydration without disturbing the underlying granulating or new epithelial tissue.

The second layer can be in contact with a third layer. The third layer is optional, but is useful to retain the first two layers in place, to serve as a barrier to microbial infection, and to control the transmission of fluid into and out of the dressing. The third layer can be a thin film, and such layer may also be incorporated into a composite dressing as a film layer.

The subject dressing can be provided in any one of a number of alternative configurations. By way of example, and not wishing to be bound to these embodiments, several alternative embodiments of the subject dressing can be described with reference to the figures shown in the attached drawings, as follows:

A. FIG. 1 shows a first layer comprising a bioabsorbable scaffold material (10) disposed adjacent a wound site (65) in the tissue of a patient (60). The first layer is covered by a second layer of an absorbent barrier material (20).

Figure 2:
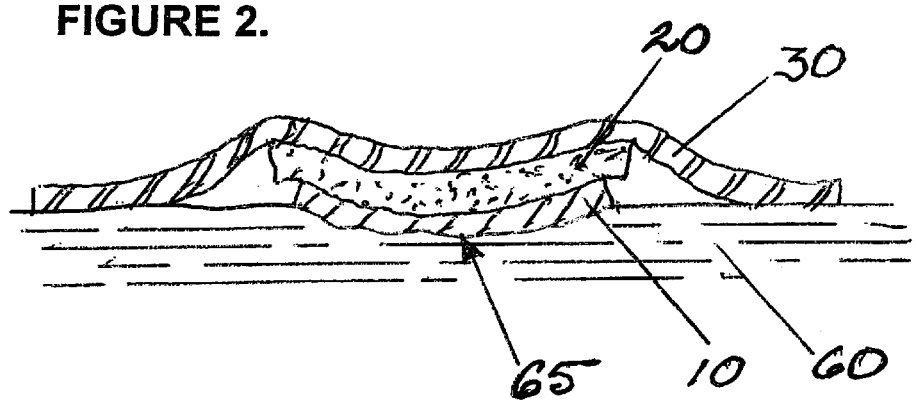
FIG. 2 illustrates a cross-sectional view of a dressing of the present invention having bioabsorbable scaffold material disposed adjacent a wound bed, and next having a layer of an absorbent barrier material, and then a layer of a breathable, water-repellant film having an adhesive on one side to adhere the dressing to the skin.

B. FIG. 2 illustrates a dressing that includes a first layer comprising a bioabsorbable scaffold material (10) that is disposed adjacent a wound site (65) in the tissue of a patient (60). The first layer is covered by a second layer of an absorbent barrier material (20), and the second layer is covered by a third layer of a breathable film material (30). The third layer can be faced with an adhesive that binds the third layer to the second layer. If desirable, the third layer can extend past the edges of the first and second layers on two or more sides to serve as a method to adhere the dressing to the patient. As an alternative, the third layer can be formed from a transparent film of a breathable material that can transmit liquid peripherally to the edge of said third layer, but which layer is adapted to serve as a barrier to cell adhesion and penetration.

Upon application to a wound, the scaffold material (10) can conform to the surface of the wound bed (65), thereby minimizing the amount of free space between the wound bed and the dressing.

Figure 3:
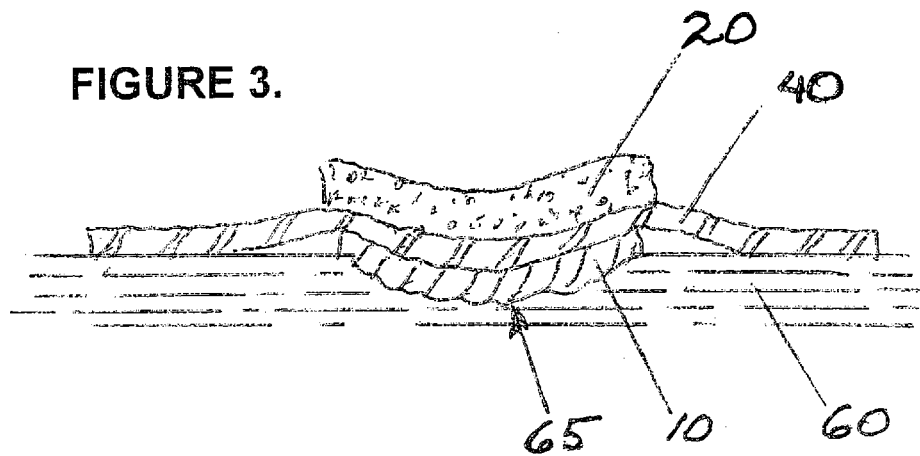
FIG. 3 illustrates a cross-sectional view of a dressing of the present invention similar to that shown in FIG. 2, except that the relative positions of the layer of absorbent barrier material and the film layer are reversed. Here, however, the film layer comprises a transparent film material capable of transmitting liquid, but which layer serves as a barrier for cell penetration and adhesion and which can also have an adhesive on one side to adhere the dressing to the skin.

C. The structure shown in FIG. 3 is similar to that described above in "B", except the position of the second layer and the third layer are reversed, and the second layer is now composed a transparent film (40) that can transport liquid, but which is adapted for serving as a barrier for cell adhesion and penetration. The second layer film also serves as a barrier to microbial infection. This structure would permit the absorbent barrier material to be replaced as needed without causing trauma to the wound site/skin because it is attached only to the third layer (the film layer). This configuration is shown in FIG. 3.

Figure 4:
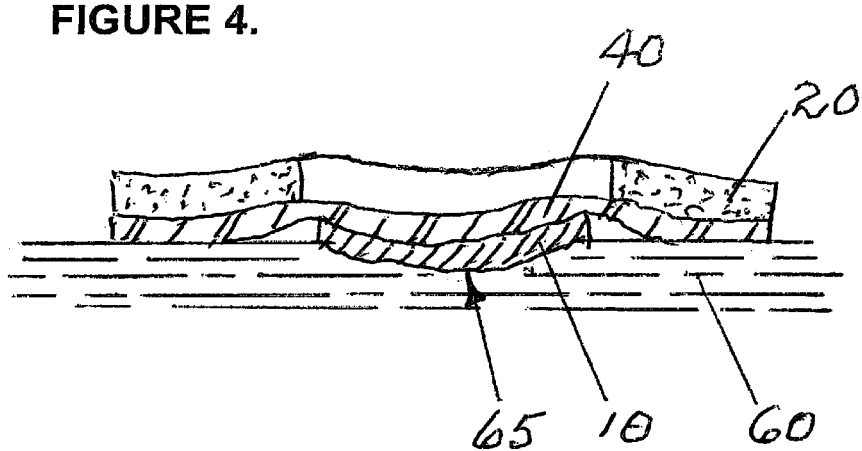
FIG. 4 illustrates a cross-sectional view of a dressing of the present invention having bioabsorbable scaffold material disposed adjacent a wound bed, and next having a layer of a transparent film material capable of transverse wicking of liquid to its periphery, which layer is adapted for serving as a barrier to cell adhesion and penetration and which can also have an adhesive on one side to adhere the dressing to the skin, and then having a layer of absorbent barrier material around the periphery of the dressing, leaving a viewing window over the wound.
Figure 5:
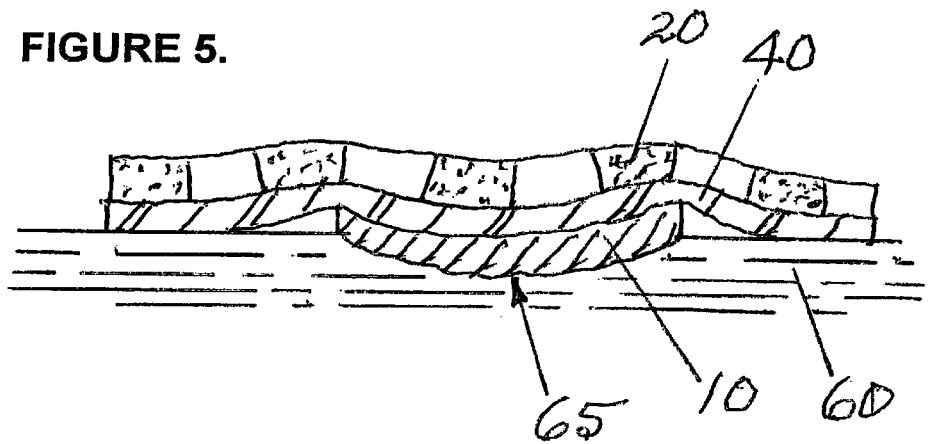
FIG. 5 illustrates a cross-sectional view of a dressing of the present invention that is similar to the dressing shown in FIG. 4, except that the layer of absorbent barrier material is in the form of a continuous web having holes therethrough.

D. FIG. 4 illustrates a dressing that includes a first layer comprising bioabsorbable scaffold material (10) that is positioned adjacent the wound bed (65). Over this layer is positioned an adhesive, breathable, transparent film (40) that can transport liquid and thereby can wick away exudate to the perimeter of the wound. An absorbent barrier material (20) is then positioned as a discontinuous third layer around the perimeter of the wound. In this embodiment, the transparent film (40) is not completely covered by the absorbent barrier material (20), thereby permitting the underlying scaffold (10) to be visible for inspection. This would permit visual monitoring of the healing process. A variation of this configuration, shown in FIG. 5, is the provision of the absorbent barrier material (20) as a "web", or "net", with holes through which the transparent film (40) can be seen.

Figure 6:
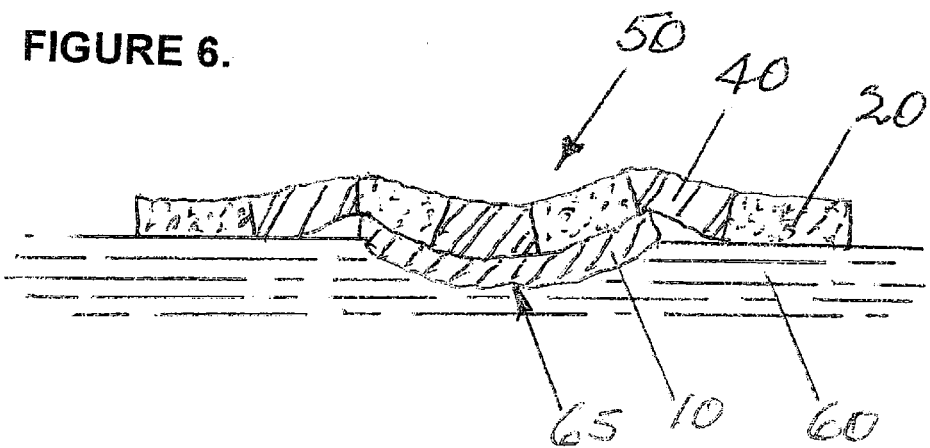
FIG. 6 illustrates a cross-sectional view of a dressing of the present invention having bioabsorbable scaffold material disposed adjacent a wound bed and having a layer composed of segments of absorbent barrier material interspersed with segments of transparent film material capable of transverse wicking of liquid to its periphery, which can also serve as a barrier for cell penetration and adhesion.
Figure 7A:
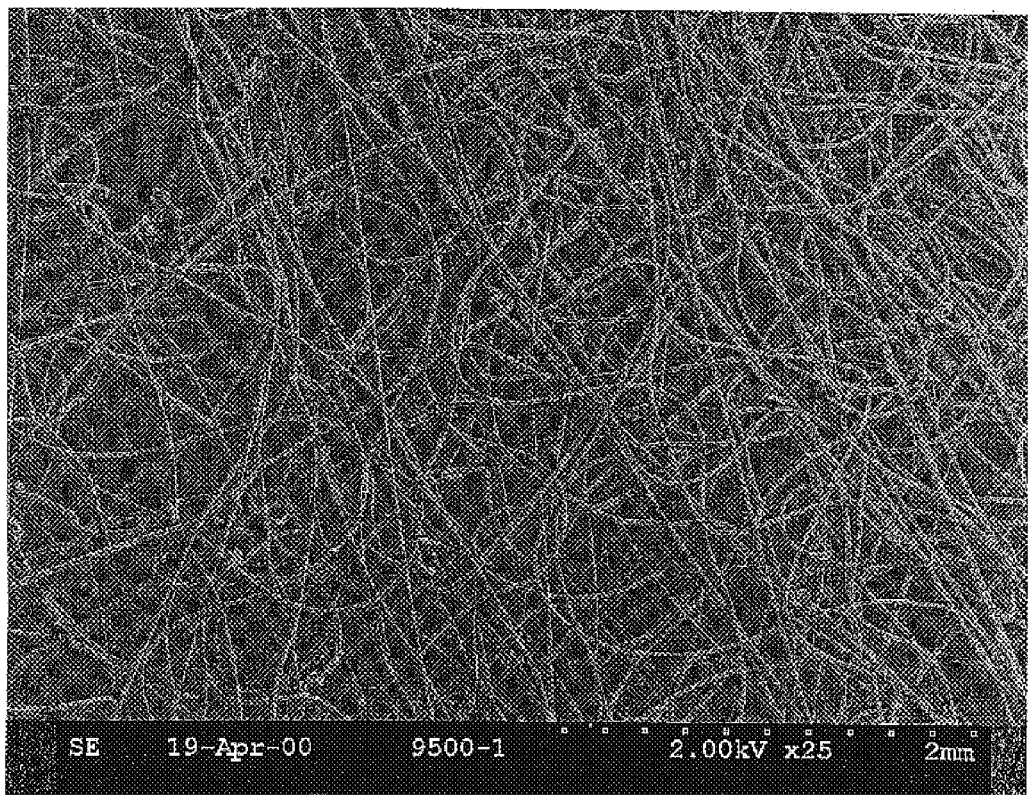
FIG. 7 shows scanning electron microscopic images of the surface of bonded carded web (BCW) surge material of poly(lactic acid) fibers at (a) 25×magnification and (b) 100×magnification.
Figure 7B:
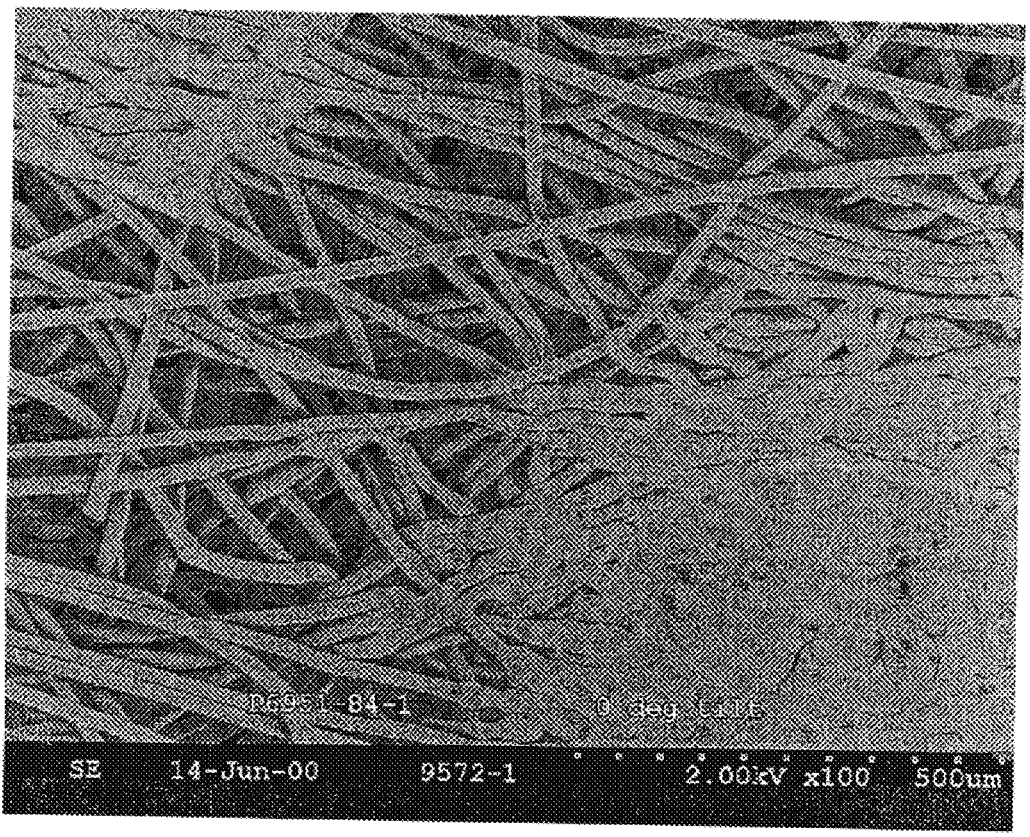

E. The embodiment shown in FIG. 6 is a variation of "D", where the absorbent barrier material (20) and the material used for the transparent film layer (40) are interspersed into a layer having a "waffle" type design (50), where each area segment comprises a portion of absorbent barrier material (20) surrounded by a boundary of the transparent film material (40). In this design, it is believed that the underlying scaffold (10) would still be visible but because the absorbent second layer is no longer limited to the perimeter of the whole dressing, absorbency would be increased. Furthermore, the dressing could easily be cut into any desired shape while retaining both the transparent film material (40) and the absorbent second layer (20) no matter what size or shape the dressing was cut into.

As described above, the subject dressing can also be supplied as a stand-alone first layer. The porous material could be prepared such that its pores on one side (the side to be positioned adjacent the wound bed) would be in the 50–400 micron range for optimal cell migration, while pores on the opposite side would be much smaller (1–10 micron range) to act as a barrier to cell growth.

F. In an alternative embodiment of the configuration described above in "B", the first layer comprises the bioabsorbable scaffold material, but this layer is covered with a coating or film of a polymeric material that acts as a barrier to cell growth and can transmit water, but that will slowly dissolve in water under the conditions of the wound site. The first layer and the barrier layer are then covered by a third layer of absorbent material and/or a breathable film. In this embodiment, the coating or film of polymeric material acts as the barrier to cell growth, and the absorbent material is not required to have such capability.

It is desirable that the subject dressing be sterile at the time of use, and the dressing can be sterilized by any appropriate sterilizing method that is known in the art. By way of example, the present dressings may be sterilized by an appropriate sterilizing cycle using ethylene oxide as a sterilizing agent. Radiation sterilization may also be used.

When the subject dressing is stored, its sterility should be protected and the dressing itself should be protected from ambient moisture. If the absorbent barrier layer is to be stored in a hydrated or partially hydrated state, that layer should be isolated from the scaffold material to prevent any degradation of the scaffold material prior to application to a wound. As an alternative, the entire dressing may be stored in a dry form and, if desirable, the absorbent barrier layer may be totally or partially hydrated by an appropriate sterile solution just prior to application to a patient. With suitable storage conditions, it is believed that the present dressing may be stored for a period of up to one or two years or more.

The subject dressing can be used in any manner in which similar dressing are used. The components of the subject dressing can be placed upon a wound separately to form a complete dressing of the present invention, or they can be formed into a unitary multilayer dressing that can be applied to a wound in a single step.

When the first layer, or first and second layers are placed on a wound prior to the addition of a covering film, they can be cut to fit the wound, or to form any shape or size that is desirable. After the application of such layer(s), a covering film layer (third layer) may be applied if desirable to bind the dressing together and to adhere the dressing to the patient.

The subject dressing can be applied to an animal or human patient and may be used on almost any type of wound in which the skin is broken or abraded and from which body fluids, such as serum, blood, or wound exudate are released. The subject dressing is particularly useful for dressing chronic wounds and burn wounds. The following examples describe various embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples.

General Procedures

In the examples, all percentages are given on a weight basis unless otherwise indicated. All molecular weights are given on a weight-average basis, unless otherwise noted.

EXAMPLE 1

This example illustrates the production of a scaffold material of poly(lactic acid) fibers.

Figure 8A:
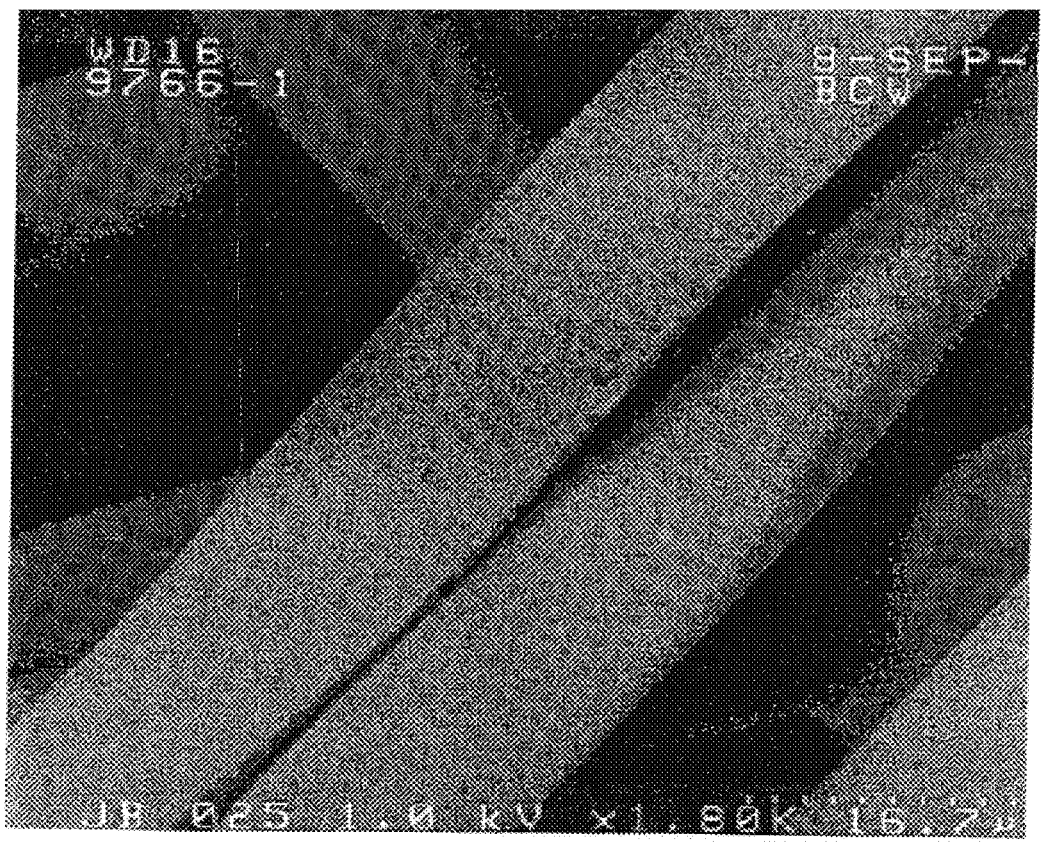
FIG. 8 shows scanning electron microscopic images of the surface of BCW surge material of poly(lactic acid) fibers (a) after water washing (at 1,000×magnification), and (b) after the washed fibers were coated with hyaluronate followed by a chitosan formulation.
Figure 8B:

The porosity and degradation characteristics were measured for poly(lactic acid) (PLA) bonded carded web (BCW) liner (available from Kimberly-Clark Co., Neenah, Wis.) and for PLA surge material (a non-woven material having a high degree of void space to accommodate high liquid loads, provided by Kimberly-Clark Co., Neenah, Wis.), and a spunbond PLA (provided by Cargill Dow L.L.C., located in Minnetonka, Minn.). Based on porosity, integrity and availability, the PLA BCW liner was selected for further testing. FIG. 8 shows SEM photomicrographic images of this material at (a) 1,800×magnification and (b) at 1,000× magnification, and illustrates the open, non-woven structure of the PLA fibers. This material, as well as the other two, was more hydrolytically stable than would normally be desirable (does not degrade after almost 3 months in normal saline at room temperature), but it was believed that the rate of bioabsorbability could be controlled to match desired levels by adjusting the degree of polymerization and other pertinent parameters of the PLA.

To effectively reduce the pore size of the material and increase its thickness to that approximating the thickness of human dermis (about 1–2 mm), four cross-laid sheets of the liner were laminated together with a certain pattern using a hot press. Separately, four cross-laid sheets of the liner material were ultrasonically bonded. By comparing SEM images of a single sheet of the material with four cross-laid and laminate sheets, it was apparent that cross-orientation was useful to create a tighter, less-oriented fiber pattern for the scaffold material.

EXAMPLE 2

This illustrates the preparation of a scaffold material having PLA fibers coated with hyaluronate and chitosan niacinamide ascorbate.

Bicomponent fibers (1.5 denier) consisting of a PLA core and a less crystalline and more degradable PLA sheath were obtained from Fiber Innovations Technology, Johnson City, Tenn. These fibers were mixed with 3 denier monofilament PLA fibers in a 60:40 weight ratio and fabricated into 1.5 osy bonded carded web (BCW). Three rolls of the BCW were then laminated together by ultrasonic bonding using the Evolution pattern to form a 3-ply laminated BCW.

A laminated sheet of 3-ply BCW was cut into circular discs using a 2 ⅛" arch punch. The discs were placed into 2 liters of distilled water with slow stirring for 24 hours to remove the finish applied to the fibers when they were fabricated. The discs were then air dried. An SEM photomicrographic image of the washed, laminated sheet is shown in FIG. 9(a).

Several washed and dried discs were placed in 0.5% buffered sodium hyaluronate (HA) solution in water for 10 minutes. The discs were then dried in air for one hour, followed by drying in a convection oven at 40° C. for one hour. The discs were then placed in the HA solution for one minute, air-dried for 30 minutes, and oven-dried for 30 minutes. The re-wetting with HA and drying steps were then repeated one time.

The discs were then placed in 2 liters of distilled water for 2 minutes to remove excess HA and salt (from buffer), and air-dried overnight followed by oven drying at 40° C. for one hour. Some discs were then coated with a chitosan salt (available from Vanson, Inc., Redmond, Wash.) by dipping the HA-coated discs into a solution of the chitosan salt for one minute. It was noted that some precipitate was formed during the time that the discs were in the chitosan salt solution. The discs were air-dried overnight and then oven dried at 40° C. for four hours. FIG. 9(b) is an SEM micrographic image of laminated BCW coated with HA and then with the chitosan salt. It is noted that bridges formed between fibers and whitish-colored areas (less electron-dense on SEM) appeared on some fibers. This was taken to indicate that a coating of the chitosan salt had actually been formed on the fibers.

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions without departing from the scope of the invention, it is intended that all matter contained in the above description and shown in the accompanying drawings shall be interpreted as illustrative and not in a limiting sense. These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole and in part. Furthermore, those of ordinary skill in the art will appreciate that the foregoing description is by way of example only, and is not intended to limit the invention so further described in such appended claims. Therefore, the spirit and scope of the appended claims should not be limited to the description of the preferred versions contained therein.

What is claimed is:

1. A wound dressing comprising:
   (a) a first layer located adjacent the wound and which comprises a fibrous nonwoven material that is bioabsorbable, has pores in the range of 50–400 microns in size, and is adapted for serving as a scaffold for cell attachment and proliferation; and
   (b) a second layer which is in contact with the first layer and which comprises an absorbent, gel forming material adapted for serving as a barrier to cell adhesion and penetration.

2. The dressing according to claim 1, comprising, in addition,
   (c) a third layer which is in contact with the second layer and which comprises a material that is penetrable to vapor but acts as a barrier to the transmission of liquid and microorganisms.

3. The dressing according to claim 1, wherein the fibers that are present in the nonwoven material are melt-spun fibers.

4. The dressing according to claim 3, wherein the melt-spun fibers are fabricated by a method selected from the group consisting of bonded carded web, spunbond and meltblown.

5. The dressing according to claim 1, wherein the material that is bioabsorbable, porous and is adapted for serving as a scaffold for cell attachment and proliferation comprises a material selected from the group consisting of poly(lactic acid), poly(glycolic acid), copolymers of lactic and glycolic acids, poly(ether-co-esters), poly(hydroxybutyrate), copolymers of lactic acid and ε-aminocapronic acid, lactide polymers, copolymers of poly(hydroxybutyrate) and 3-hydroxyvalerate, polyesters of succinic acid, cross-linked hyaluronic acid and cross-linked collagen.

6. The dressing according to claim 5, wherein the bioabsorbable scaffold material is capable of being bioabsorbed within a period of from about 1 week to about 6 months.

7. The dressing according to claim 6, wherein the bioabsorbable scaffold material is capable of being bioabsorbed within a period of from about 1 month to about 2 months.

8. The dressing according to claim 5, wherein the first layer comprises in addition at least one material selected from the group consisting of a hyaluronan, collagen, laminin, fibronectin, growth factor, integrin, sodium hyaluronate, chitosan, niasinamide ascorbate, drug, vitamin, therapeutic peptide, and combinations thereof.

9. The dressing according to claim 6, where the first layer is from about 1 mm to about 10 mm in thickness.

10. The dressing according to claim 9, where the first layer is from about 1 mm to about 2 mm in thickness.

11. The dressing according to claim 1, wherein the absorbent, gel forming material adapted for avoiding cell adhesion and penetration comprises a hydrogel.

12. The dressing according to claim 11, wherein the absorbent, gel forming material has pores that are less than about 10 microns in size when said material is in a hydrated state.

13. The dressing according to claim 12, wherein the absorbent, gel-forming material is selected from a group that consists of polyacrylate hydrogels, polyurethane hydrogels, cross-linked poly(ethylene oxide) hydrogels, carboxymethylcellulose hydrogels, and hydrocolloid type materials.

14. The dressing according to claim 11, wherein the second layer comprises in addition a material selected from the group consisting of vitamins, proteins, peptides, growth factors, drugs, nutrients, antibiotics, and any combination thereof.

15. The dressing of claim 1, having in addition an adhesive, breathable film of a material that can transmit liquid but which is adapted for serving as a barrier to cell adhesion and penetration located between the first layer and the second layer.

16. A wound dressing comprising:
   (a) a first layer located adjacent the wound and which comprises a material that is bioabsorbable, porous and adapted for serving as a scaffold for cell attachment and proliferation;
   (b) a second layer comprising a transparent film of a breathable material that can transport liquid peripherally to the edges of said second layer, but which is adapted for serving as a barrier to cell adhesion and penetration; and
   (c) a third layer which is in contact with the second layer and which comprises an absorbent material.

17. The dressing according to claim 16, wherein the third layer is located on the periphery of the second layer so that the portion of the second layer that is located over the wound is not covered by the third layer.

18. The dressing according to claim 16, wherein the third layer is in the form of a net having areas through which portions of the second layer that are located over the wound are not covered by the third layer.

19. The dressing of claim 1, having in addition a coating or film of a polymeric material that acts as a barrier to cell growth and can transmit water, but that will slowly dissolve under the conditions of the wound site, which coating or film is located between the first layer and the second layer.

20. A method for treating a wound comprising applying to the wound a wound dressing comprising:
   (a) a first layer located adjacent the wound and which comprises a fibrous nonwoven material that is bioabsorbable, has pores in the range of 50–400 microns in size, and is adapted for serving as a scaffold for cell attachment and proliferation; and
   (b) a second layer which is in contact with the first layer and which comprises an absorbent, gel forming material adapted for serving as a barrier to cell adhesion and penetration.

21. The method according to claim 20, wherein the dressing comprises, in addition,
   (c) a third layer which is in contact with the second layer and which comprises a material that is penetrable to vapor but acts as a barrier to the transmission of liquid and microorganisms.

22. A method for treating a wound comprising applying to the wound a wound dressing comprising a layer located adjacent the wound which comprises a nonwoven fabric having pores of from about 50 microns to about 400 microns in size and comprising a material selected from the group consisting of poly(lactic acid), poly(glycolic acid), copolymers of lactic and glycolic acids, poly(ether-co-esters), poly(hydroxybutyrate), copolymers of lactic acid and ε-aminocapronic acid, lactide polymers, copolymers of poly (hydroxybutyrate) and 3-hydroxyvalerate, polyesters of succinic acid, and cross-linked hyaluronic acid.

23. A method for treating a wound comprising applying to the wound a wound dressing comprising:
(a) a first layer located adjacent the wound and which comprises a nonwoven fabric having pores of from about 50 microns to about 400 microns in size and comprising a material selected from the group consisting of poly(lactic acid), poly(glycolic acid), copolymers of lactic and glycolic acids, poly(ether-co-esters), poly(hydroxybutyrate), copolymers of lactic acid and ε-aminocapronic acid, lactide polymers, copolymers of poly(hydroxybutyrate) and 3-hydroxyvalerate, polyesters of succinic acid, cross-linked hyaluronic acid and cross-linked collagen;
(b) a second layer which is in contact with the first layer and which comprises a hydrogel having pores of less than about 10 microns in size when the hydrogel is in a hydrated state; and
(c) third layer which is in contact with the second layer and which comprises a material that is penetrable to vapor but acts as a barrier to the transmission of liquid and microorganisms.

* * * * *

UNITED STATES PATENT AND TRADEMARK OFFICE
CERTIFICATE OF CORRECTION

| | | |
|---|---|---|
| PATENT NO. | : 7,041,868 B2 | |
| APPLICATION NO. | : 10/026292 | |
| DATED | : May 9, 2006 | |
| INVENTOR(S) | : Greene et al. | |

It is certified that error appears in the above-identified patent and that said Letters Patent is hereby corrected as shown below:

Column 16, line 65 (Claim 22) "comprises a nonwcven fabric" should read --comprises a nonwoven fabric--

Signed and Sealed this

Twenty-eighth Day of August, 2007

JON W. DUDAS
*Director of the United States Patent and Trademark Office*